United States Patent [19]

Muller

[11] Patent Number: 4,799,010
[45] Date of Patent: Jan. 17, 1989

[54] PROCESS FOR DETECTING DEFECTS ON A SURFACE BY EDDY CURRENTS AND DEVICE FOR CARRYING OUT SAID PROCESS

[75] Inventor: Jean-Louis Muller, Le Vesinet, France

[73] Assignee: Institut de Recherches de la Siderurgie Francaise, Maizieres-Les-Metz, France

[21] Appl. No.: 876,854
[22] PCT Filed: Sep. 20, 1985
[86] PCT No.: PCT/FR85/00258
§ 371 Date: May 20, 1986
§ 102(e) Date: May 20, 1986
[87] PCT Pub. No.: WO86/01896
PCT Pub. Date: Mar. 27, 1986

[30] Foreign Application Priority Data

Sep. 20, 1984 [FR] France .................. 84 14435

[51] Int. Cl.⁴ ............................................. G01N 27/90
[52] U.S. Cl. ..................................... 324/240; 324/232; 324/233; 324/242
[58] Field of Search ......... 324/225, 232, 233, 239-243, 324/235

[56] References Cited

U.S. PATENT DOCUMENTS

| 3,166,710 | 1/1965 | Schmidt | 324/242 |
| 3,286,168 | 11/1966 | Schmidt | 324/233 |
| 3,450,986 | 6/1969 | Chapman et al. | 324/235 |
| 3,535,625 | 10/1970 | Pratt | 324/233 |
| 3,763,424 | 10/1973 | Bennett, Jr. et al. | 324/239 X |
| 3,916,301 | 10/1975 | Vild et al. | 324/233 X |
| 4,322,683 | 3/1982 | Vieira et al. | 324/225 |
| 4,467,281 | 8/1984 | Davis et al. | 324/232 |
| 4,468,619 | 8/1984 | Reeves | 324/235 X |
| 4,594,549 | 6/1986 | Smith et al. | 324/242 X |
| 4,651,093 | 3/1987 | Detriche et al. | 324/233 X |

FOREIGN PATENT DOCUMENTS 0117786 9/1984 European Pat. Off. ............ 324/241

Primary Examiner—Gerard R. Strecker
Attorney, Agent, or Firm—Staas & Halsey

[57] ABSTRACT

A magnetic field is produced by way of an emitter placed close to the surface of a product to be controlled and a receiver separate from the emitter is placed, with respect to said emitter, on the one hand, in such a way as to be aligned with the emitter in a direction corresponding to the general orientation of the defects to be detected on the surface of the product, and on the other hand, so as to avoid any substantial direct influence from the eddy currents generated by the emitter when the product surface is defect-free, so that a significant signal is only picked up by the receiver in the case of a deviation of said eddy currents in its direction due to a discontinuity in the surface of the product. The invention finds an application in the detection of surface defects in semi-finished metallurgical products and in particular continuously cast steel products.

9 Claims, 4 Drawing Sheets

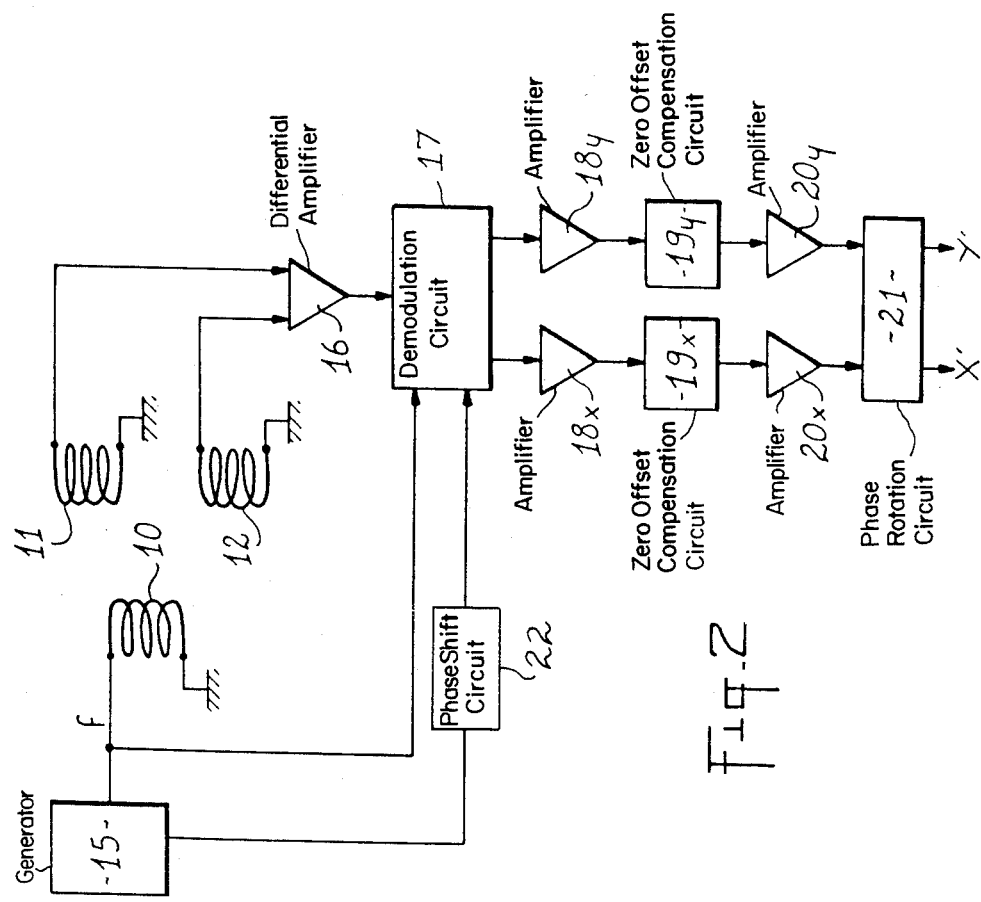
Fig. 2
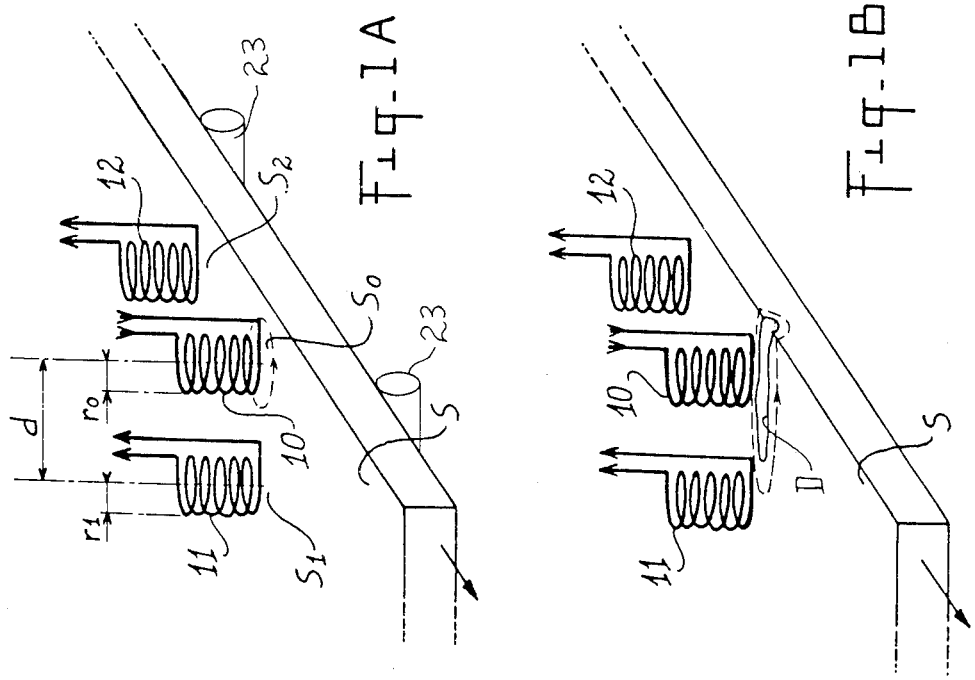
Fig. 1A
Fig. 1B

PROCESS FOR DETECTING DEFECTS ON A SURFACE BY EDDY CURRENTS AND DEVICE FOR CARRYING OUT SAID PROCESS

The present invention relates to a process for detecting defects on a surface, by eddy currents, and more particularly a process of the type whereby a magnetic field is generated by way of an emitter placed close to the surface of the product to be controlled, and a receiver separate from the emitter is placed also close to the surface of the product in order to collect a signal indicating possible disturbances in the eddy currents circulation on the surface of the product, due to defects in said surface.

The field of application of the invention is that of the detection of defects on the surface of semi-finished metallurgical products, in particular the detection of cracks on semi-finished iron and steel products such as steel slabs, blooms or billets exiting from a continuous casting installation.

Detection of surface defects by eddy currents is presently performed with double-action sensors, namely sensors in which the same winding is emitter and receiver, or as in the case of the process of the aforedescribed type, with sensors having separate functions in which the emitter and receiver windings are separate.

Sensors with separate functions permit a greater detection response, yet this is often very difficult due to a high level of noise. Indeed, in a conventional sensor with separate functions, the receiver winding or windings are placed in the acting zone of the emitter winding. Yet the response of the receiver is affected by numerous factors such as geometry, conductivity and permeability of the product, and the inevitable variation of these factors, even in the absence of actual defects, consideraly lowers the signal/noise ratio.

To improve this ratio, it is known to use differential sensors with two receiver windings before which moves the product to be controlled. Detection is achieved by processing a signal representing the difference between the signals delivered by the two receiver windings. It is then possible with the relative closeness of these two windings to overcome the effect of slow variations in the structure or in the characteristics of the product.

However, even with differential sensors, it may still prove difficult to obtain a reliable detection because of a high noise level. This is so for example, with the detection of cracks on a slab, particularly because of the presence of surface irregularities (wrinkle or waviness formations) which disturb the field without actually constituting defects. Also, and speaking more generally, the detector response is not only affected by variations in the geometry of the product, but also by conductivity and permeability variations due to localized heterogeneities, and also by distance variations between receiver and product.

Therefore, it is the object of the invention to propose a process for detecting surface defects by eddy currents in which an important improvement of the signal/noise ratio is obtained over the previous processes.

This object is reached with a process of the type described hereinabove and in which, according to the invention, the receiver is placed with respect to the emitter, on the one hand, in such a way as to be aligned with the emitter in a direction corresponding to the general orientation of the defects to be detected on the surface of the product, and, on the other hand, so as not to be substantially affected by the eddy currents generated by the emitter when the surface of the examined product is defect-free, so that a significant signal is collected by the receiver only in case of deviation of the eddy currents in its direction due to a discontinuity on the surface of the product.

The position of the receiver in a zone situated outside the zone of direct influence of the emitter presents many advantages.

First of all, anything liable to disturb the eddy currents has no effect on the detection as long as these currents remain confined to the zone of the surfaces facing the emitter. For example, local variations of conductivity or permeability cannot hinder the detection. In the same way, to some extent, the presence of wrinkles or waviness brings less disturbances.

Then, the simple fact of collecting a signal on the receiver is enough to indicate the existence of a defect. Variations of distance between the received and the product are less troublesome and it is quite possible to do without a differential detection. It should be noted that, according to the invention, the signal produced by the detector, influenced by the eddy currents deviated by the defect, is not compared with the signal produced by another detector influenced by the eddy currents generated by the same emitter, as this is the case with the differential sensors of the prior art.

Understandably, the detected defects are those in the form of discontinuity of surface which have a certain dimension in the direction of alignment of the emitter and receiver. Thus, in the case of a moving slab, an emitter and a receiver, aligned transversely with respect to the product, will permit the detection of defects such as crevasses, splits and cracks oriented principally crosswise. The detection of defects of the same type, but oriented principally longitudinally, require an emitter and a receiver aligned in the longitudinal direction of the product.

A plurality of receivers can thus be operationally coupled to the same emitter for detecting defects oriented in different directions, the signals emitted by the receivers when the presence of a defect has been detected, being then processed separately.

Another object of the invention is to propose a device for carrying out the above process.

This object is reached with a device for detecting defects by eddy currents on the surface of semi-finished metallurgical products, of the type comprising an emitter designed to generate a magnetic field close to the surface of a product to be controlled, and a receiver separate from the emitter and designed to collect a signal indicating possible disturbances of the eddy current on the surface of the product, due to defects present on said surface, device wherein, according to the invention, the receiver is spaced apart from the emitter so as not to be directly influenced by the magnetic field generated by said emitter, whereby a significant signal is collected by the receiver only in the case of deviation of the eddy currents in the direction of the receiver due to a discontinuity on the surface of the product.

The invention will be more readily understood on reading the following description with reference to the accompanying drawings, in which:

FIGS. 1A and 1B illustrate very diagrammatically a detection process according to the invention, respectively with and without a defect on the surface of a product, being controlled.

FIG. 2 is a diagram of the circuit processing the signals from the receiver windings of FIG. 1.

Figure 3A:
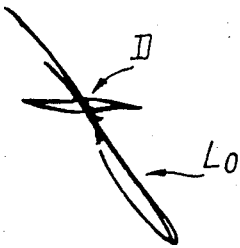
FIGS. 3A to 3D illustrate variations in the phase diagram of signals obtained with the different detection devices, such as that shown in FIG. 1.

The detection device diagrammatically illustrated in FIG. 1A comprises an emitter 10, a first receiver 11 and a second receiver 12 situated opposite and close to the surface S of a metallic product to be controlled, caused to be moving before the detector device by a moving or conveying apparatus 23.

The emitter 10 is constituted by a winding of axis perpendicular to the surface S and supplied with an alternating current of preset fixed frequency f. An alternating magnetic field is thus produced, this field causing the circulation of eddy currents confined essentially in that part $S_O$ which is defined by the projection on said surface of the coil 10.

Receivers 11 and 12 are also constituted by windings having axes perpendicular to the surface S.

Winding 11 is spaced apart from winding 10 and is always opposite a zone $S_1$ of the surface S which is entirely outside the part of surface $S_0$. Thus, normally, the circulation of eddy currents in surface part $S_0$ does not induce any signal in winding 11.

Winding 11 is positioned with respect to winding 10 as a function of the type of defect to be detected. Indeed, the invention is based on the fact that, when there is a discontinuity of the surface in the influence zone of the emitter, the eddy currents are deviated in order to avoid said discontinuity and are no longer confined in the surface zone facing the emitter.

Since the receiver is situated with respect to the emitter in the direction in which the currents are deviated, then it will deliver a signal only in the presence of a defect.

Supposing that the product to be controlled is a product in strip form, with possible surface defects in the form of transversal crevasses, splits or cracks, the axes of windings 10 and 11 are situated inside the same transversal plane with respect to the moving product. When the defects to be detected start on one edge of the product, the emitter 10 is placed opposite the part of surface of the product which is adjacent the said edge. FIG. 1B shows the passage of a defect D in the detection zone, causing the deviation of the eddy currents in the direction of the receiver.

In the same way as winding 11, winding 12 is spaced apart from the coil 10 and is always opposite a zone $S_2$ of the surface S which is entirely outside the part of surface $S_0$. The axes of the coils 10 and 12 are in a longitudinal plane, hence perpendicular to the general direction of the transverse defects to be detected. Thus receiver 12 is never influenced by the emitter whether directly or indirectly in case of transverse defects. The coil 12 is used as a reference in order to eliminate the influence of ambient magnetic fields in the signal collected by the coil 11, owing to a differential connection.

Understandably, the detection device according to FIG. 1A can be used for detecting longitudinal defects by inversing the parts played by receivers 11 and 12.

As illustrated in FIG. 2, the emitter winding 10 is energized by means of a generator 15 and the signals received by the receiver windings 11 and 12 are applied to the respectively inverting and non-inverting inputs of a differential amplifier 16. The output signal of said amplifier is demodulated in phase and in quadrature by means of a demodulation circuit 17 which in fact receives, on the one hand, the output signal of the generator 15 and, on the other hand, this same output signal phase-shifted by 90° by a phase shift circuit 22. The demodulated signals outputted from circuit 17 are processed in two parallel tracks each comprising, a first amplification stage 18x, 18y, a circuit 19x, 19y for zero offset compensation and a second amplification stage 20x, 20y with adjustable gain. The amplitudes of signals X and Y in output of stages 20x and 20y are an indication of the "active" and "reactive" components of the output signal of amplifier 16, after demodulation in phase and in quadrature. It will be noted that the above-described circuits 17 to 20x and 20y form an assembly known per se and used in detection apparatus employing eddy currents, such as for example the apparatus marketed by the firm PLS under the reference "Metalog" or by the firm HBS under the reference "EC 3000". It is also known to complete these circuits with a phase rotation circuit 21 receiving signals X and Y and delivering signals:

$$X' = X \cos a + Y \sin a, \text{ and}$$

$$Y' = -X \sin a + Y \cos a,$$

representative of the projections of the output signal of amplifier 16 on orthogonal axes of a reference system phase-shifted by an angle a, with respect to the output signal of generator 15. Said angle a is so selected as to obtain a maximum signal/noise ratio for one of the components X', Y'. Said component is thereafter processed, for example by comparison with a predetermined threshold, in order to give, whenever necessary, a signal indicating the presence of a defect.

A number of tests have been conducted in order to compare the results obtained according to the detection process of the invention, with the results obtained according to the prior art processes, and in order to estimate the influence of different parameters. The results of these tests are given in the form of variations of the signals obtained, represented in the phase diagram, namely the curves described by one point having the coordinate values X and Y in output of stages 20x and 20y.

Test No. 1

Figure 3B:
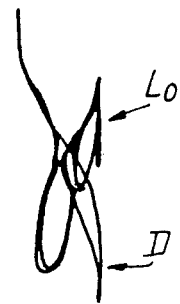
Figure 3C:
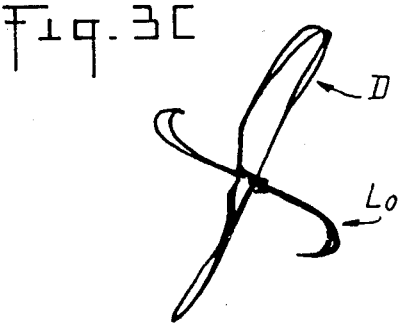
Figure 3D:
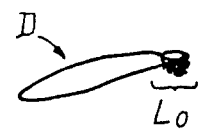
Figure 4A:
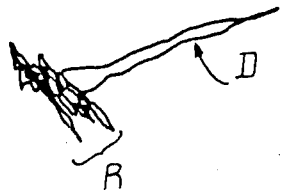
FIGS. 4A to 4D illustrate variations in the phase diagram of signals obtained with the device of FIG. 1, for different values of the distance between emitter and transversal receiver.
Figure 4B:
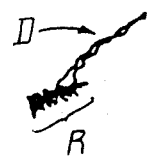
Figure 4C:
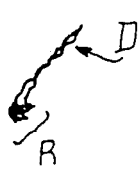
Figure 4D:

FIGS. 3A to 3D illustrate the results obtained with different detection sensors when an upward movement is imposed on the receiver sensors with respect to the product surface ("lift-off"):

FIG. 3A corresponds to the use of two conventional double-action sensors in the form of flat windings;

FIG. 3B corresponds to the use of conventional double-action sensors in the form of ferrite windings; and FIG. 3C corresponds to the use of conventional sensors with separate functions in the form of ferrite windings; and FIG. 3D corresponds to the use of the detection device according to the invention illustrated by FIG. 1, windings 10, 11 and 12 being flat windings of 10 mm diameter and the axis of windings 11 and 12 being apart from the axis of winding 10, and both of 20 mm.

In every case, the emitter energizing frequency is equal to 20 kHz.

In FIGS. 3A to 3D, the curves D represent the influence of the defect and the curves LO the influence of the upward displacement of the receivers with respect to the product surface. Said curves clearly show that the influence of variation of position of the receiver heightwise becomes quite negligible with the process according to the invention.

Test No. 2

FIGS. 4A to 4D illustrate the results obtained with the detection device according to FIG. 1 by varying the distance d between the axis of windings 10 and 11, windings 10, 11 and 12 being flat windings of 11 mm diameter and the excitation frequency being 20 kHz.

Measurements were taken on a slab presenting a transversal crack and wrinkles. Curves D represent the defect and curves R the wrinkles. FIGS. 4A to 4D correspond to values of d respectively equal to 20, 25, 30 and 35 mm.

It is observed, and this is normal, that the influence of the defect and the influence of the wrinkles decrease as the distance d increases. There is no substantial increase of the signal/noise ratio when distance d passes from 20 mm to 35 mm and, in every case, the signal corresponding to the wrinkles may be, for a large part, eliminated by a phase rotation, only the component obtained by projecting on the axis perpendicular to the general direction of the elongated lobes constituting the curves R.

In general, it is required to place the receiver at a sufficiently long distance from the emitter to avoid any substantial direct influence from it, and at a sufficiently short distance, to collect a significant signal, given the length of the defects to be detected. Taking for example the detection of cracks on a slab of steel obtained by continuous casting, satisfactory results are obtained when the value $d-(r_o+r_l)$ is between 0 and 25 mm, $r_o$ and $r_l$ being the radii of windings 10 and 11.

Test No. 3

Figure 5:
FIGS. 5A to 5E illustrate variations in the phase diagram of signals obtained with the device of FIG. 1 for different values of the emitter energizing frequency.
Figure 5B:
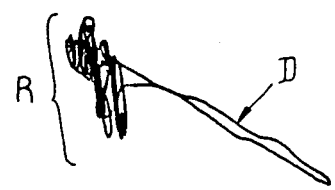
Figure 5C:
Figure 5D:
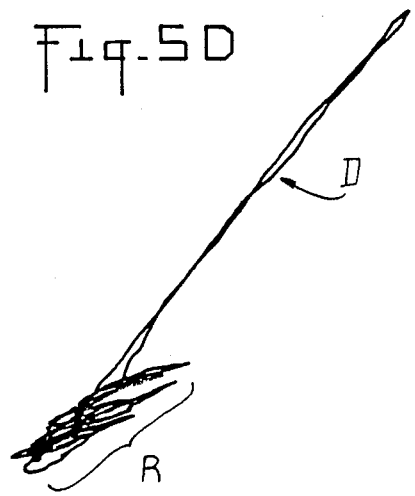
Figure 5E:
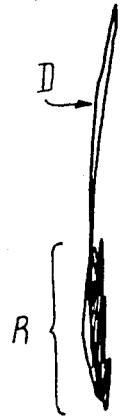

FIGS. 5A and 5E illustrate the results obtained in conditions that differ from those of Test No. 2, on the one hand, in that distance d is kept constant and equal to 20 mm, and on the other hand, in that frequency of excitation f of emitter 10 is respectively equal to 10, 20, 50, 100 and 250 kHz.

A high enough frequency is desirable for the sensor to be fairly sensitive and for the wrinkle effect to keep a relatively constant phase, permitting its elimination by phase projection. A frequency at least equal to 20 kHz seems in this case to be preferable.

However, the "skin effect" increasing with the frequency, any transversal geometrical discontinuity tends to create the same signal; the relative amplitude of the "wrinkle" signal increases and the phase tends to become the same for the signal "wrinkles" and for the signal "cracks", thus preventing the improvement of the signal/noise by phase projection. It is not desirable to exceed the value of 100 kHz, and preferably even the value 50 kHz.

Figure 6:
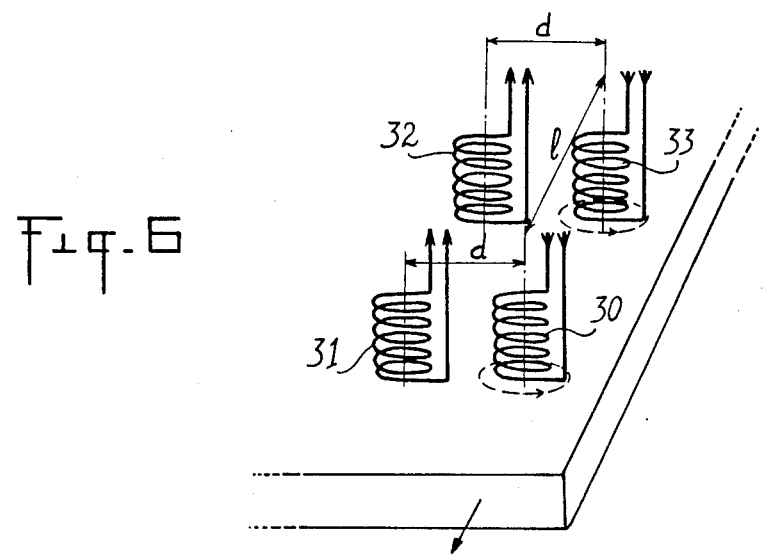
FIG. 6 illustrates very diagrammatically a detection device with differential sensor means according to the invention.

FIG. 6 illustrates another embodiment of the process according to the invention for carrying out an effectively differential detection.

Taking again, as an example, the detection of transversal surface defects on a moving product, two identical couples each formed of an emitter and a receiver are used and are placed one behind the other in the moving direction of the product. The first couple comprises an emitter winding 30 and a receiver winding 31 disposed in the same way as windings 10 and 11 of the device shown in FIG. 1A. The second couple further comprises an emitter winding 33 an a receiver winding 32 disposed in the same way. Thus, the axes of windings 30 and 31 are in a transversal plane which is at a distance l from the transversal plane defined by the axes of windings 33 and 32.

When a transversal defect is present, it will successively influence windings 32 and 31. The signals collected by these windings are processed in a circuit identical to that shown in FIG. 2, the emitter windings 30 and 33 being energized in parallel. In case of a defect, the differential signal presents two successive variations, successively in one direction and in the other.

The resulting detection is effectively differential since the obtained signal is symmetrical for a given defect (this is not so for the device shown in FIG. 1 which effects a pseudo-differential detection). The distance l between the emitters should be sufficient to avoid an inter-action between the emitter-receiver couples, without being too long, so that the receivers remain subject to the same ambient conditions. By way of indication, the value of l can be of the same order as the value of distance d between the axes of windings 30 (or 33) and 31 (or 32), said distance d being selected according to the criteria mentioned hereinabove relatively to the embodiment shown in FIG. 1A.

The following tests were conducted in order to compare the results obtained with the device according to FIG. 6 to the results obtained with the differential sensors of the prior art.

Test No. 4

FIGS. 7A to 7D illustrate the results obtained in the phase diagram with the different detection devices when detecting a crack on a slab produced by continuous casting.

Figure 7A:
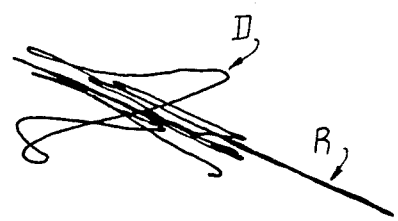
FIGS. 7A to 7D illustrate variations in the phase diagram of signals obtained with different detection devices, such as that shown in FIG. 6, in the case of a crack on a slab exiting from a continuous casting installation.

FIG. 7A corresponds to the use of a conventional sensor with separate functions, formed by windings with ferrite cores, with an excitation frequency of 5 kHz.

Figure 7B:

FIG. 7B corresponds to the use of a conventional double-action sensor, formed by windings with ferrite cores, with an excitation frequency of 13 kHz.

Figure 7C:
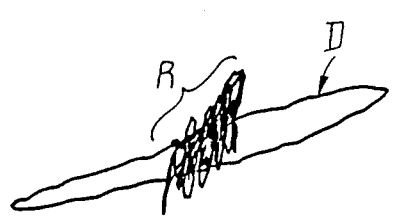
Figure 7D:

FIGS. 7C and 7D correspond to the use of a detection device according to the invention, such as that illustrated in FIG. 6. In the case of FIG. 7C, l=d=20 mm and the excitation frequency is of 20 kHz whereas in the case of FIG. 7D, l=d=30 mm and the excitation frequency is 50 kHz.

It is clear from the curves shown in FIGS. 7A to 7D that the use of the detection process according to the invention really permits a minimization of the "wrinkles" signal (curves R) over the "crack" signal (curves D).

In all the foregoing, the case considered has been that where a signal is formed to be representative of the difference between the signals delivered by the two receiver windings (pseudo-differential or effectively differential detection).

It is understood that the invention can also be used, and this is precisely one of its advantages, for effecting an absolute detection, namely by using only one emitter winding and only one receiver winding such as windings 10 and 11 of FIG. 1A. The signal picked up by the receiver winding is then directly applied to a demodulator in phase and in quadrature.

What I claim is:

1. A device for detecting defects having a general orientation on a surface of a semi-finished metallic product, said device comprising:
    an emitter situated close to the surface of the product to be examined for generating a magnetic field to cause eddy currents to be generated within a predetermined region of said surface;
    a receiver separate from said emitter and close to the surface of the product such that the receiver is aligned with the emitter in a direction corresponding to the general orientation of the defects to be detected on said surface, said receiver being spaced from said emitter so as to be outside the predetermined region and not affected by the eddy currents generated by the magnetic field produced by the emitter when the surface of the product is defect-free, and producing a significant signal when a defect in the surface of the product causes a deviation of the eddy currents in the direction of the receiver; and
    means for providing relative movement between said surface and said emitter and receiver.

2. A device according to claim 1, wherein said emitter and said receiver are windings having axes perpendicular to the surface of the product and having respective radii $r_0$ and $r_I$ such that:

$$0 < d - (r_0 + r_I) < 25 \text{ mm}$$

here d is a distance between the axis of the emitter winding and the axis of the receiver winding.

3. A device according to claim 1, further comprising:
    a second emitter placed close to and opposite a portion of the surface of the product situated outside the predetermined region of said surface opposite said emitter, for generating a second magnetic field to cause second eddy currents in a second predetermined region of said surface;
    a second receiver located close to the surface of the product and aligned with respect to the second emitter in a direction corresponding to the general orientation of defects to be detected on said surface, said second receiver being spaced from said second emitter so as to be outside the second predetermined region and not effected by the second eddy currents when the surface is defect-free and supplying a significant signal when a defect in the surface causes a deviation of the second eddy currents in the direction of the second receiver; and
    means for generating a differential signal representative of the difference between the signals supplied by said receiver and said second receiver.

4. A device according to claim 1, wherein the product is a steel slab exiting a continuous casting installation and said device is integral with the continuous casting installation.

5. A process for detecting defects having a general orientation on a surface of a semi-finished metallic product, said process comprising the steps of:
    generating a magnetic field by means of a first emitter having a winding placed in proximity to the surface of the product to be examined, said magnetic field causing eddy currents to be generated in a limited area of the surface facing the emitter winding,
    detecting the defects in the surface of the product means of at least a first receiver having a winding placed in proximity to the surface, the receiver winding being separate from the emitter winding and spaced therefrom so as to face a region of the surface outside the limited area within which said eddy currents are generated when the surface is defect-free, the receiver being aligned with the emitter in a direction corresponding to the general orientation of the defects to be detected, so that the receiver is affected by said eddy currents and produces a significant signal only when the surface of the product has a defect so that said eddy currents are deviated in the direction of the receiver, and
    imparting a relative movement between the product and an assembly formed by the emitter and the receiver.

6. A process according to claim 5, further comprising the steps of:
    generating a second magnetic field by means of a second emitter having a winding placed in proximity to the surface of the product and opposite an area of the surface located outside the area of the surface faced by the first emitter, said second magnetic field causing second eddy currents to be generated in a second limited area of the surface facing the winding of the second emitter,
    providing a second receiver having a winding placed in proximity to the surface and located with respect to the winding of the second emitter in the same way as the winding of the first receiver with respect to the winding of the first emitter, so that the second receiver produces a significant signal only when the surface of the product has a defect causing said second eddy currents to be deviated in the direction of the second receiver, and
    generating a differential signal representative of a difference between the signals respectively produced by the receivers.

7. A process according to claim 5, wherein the magnetic field produced by the emitter is an alternating magnetic field having a frequency of between 20 and 50 kHz.

8. A process according to claim 5, wherein said emitter winding and said receiver winding have axes perpendicular to the surface of the product and have respective radii $r_0$ and $r_1$ such that:

$$0 < d - (r_0 - r_1) < 25 \text{ mm}$$

where d is a distance between the axis of the emitter winding and the axis of the receiver winding.

9. A process according to claim 5 wherein the product is a semi-finished steel product in a continuous casting installation.

* * * * *